US008446576B2

(12) United States Patent
Ito et al.

(10) Patent No.: US 8,446,576 B2
(45) Date of Patent: May 21, 2013

(54) CARRIER CONCENTRATION MEASURING DEVICE AND CARRIER CONCENTRATION MEASURING METHOD

(75) Inventors: Hiromasa Ito, Saitama (JP); Seigo Ohno, Saitama (JP); Akihide Hamano, Ibaraki (JP)

(73) Assignees: Riken, Saitama (JP); Furukawa Co., Ltd., Tokyo (JP)

( * ) Notice: Subject to any disclaimer, the term of this patent is extended or adjusted under 35 U.S.C. 154(b) by 416 days.

(21) Appl. No.: 12/747,284

(22) PCT Filed: Dec. 11, 2008

(86) PCT No.: PCT/JP2008/003715
§ 371 (c)(1),
(2), (4) Date: Jun. 10, 2010

(87) PCT Pub. No.: WO2009/078149
PCT Pub. Date: Jun. 25, 2009

(65) Prior Publication Data
US 2010/0271618 A1 Oct. 28, 2010

(30) Foreign Application Priority Data
Dec. 14, 2007 (JP) ................................. 2007-323395

(51) Int. Cl.
*G01J 3/00* (2006.01)
(52) U.S. Cl.
USPC ............................................ 356/51; 356/448
(58) Field of Classification Search
USPC .................. 356/51, 73, 445, 448, 432–444
See application file for complete search history.

(56) References Cited

U.S. PATENT DOCUMENTS

| 6,211,961 B1* | 4/2001 | Maris ............................. 356/432 |
| 2007/0235650 A1* | 10/2007 | Federici et al. ............. 250/341.8 |
| 2007/0257216 A1 | 11/2007 | Withers et al. |

(Continued)

FOREIGN PATENT DOCUMENTS

| JP | 2002-005828 | 1/2002 |
| JP | 2004-003902 | 1/2004 |

(Continued)

OTHER PUBLICATIONS

K.A. Maslin, C. Patel and T.J. Parker, "Far-Infrared Optical Constants of a Selection of Zincblende Structure Crystlas at 300K", Infrared Physics, vol. 32 (1991), pp. 303-310.

(Continued)

*Primary Examiner* — Tarifur Chowdhury
*Assistant Examiner* — Michael P Lapage
(74) *Attorney, Agent, or Firm* — Rankin, Hill & Clark LLP

(57) ABSTRACT

A nondestructive carrier concentration measuring device (100) includes: a storage unit (101) that stores a correlation between the reflectance of an inorganic compound semiconductor against terahertz light and a carrier concentration; a light radiation unit (103) that irradiates the terahertz light (105) to the inorganic compound semiconductor as a sample; a detection unit (109) that detects reflected light (108) of the inorganic compound semiconductor against the irradiated terahertz light (105); a reflectance calculation unit (111) that compares the irradiated terahertz light (105) with the reflected light (108) and calculates an actual measurement value of the reflectance of the inorganic compound semiconductor; and a read unit (113) that refers to the stored correlation and reads the carrier concentration of the sample corresponding to the actual measurement value of the reflectance.

17 Claims, 12 Drawing Sheets

U.S. PATENT DOCUMENTS

| | | | |
|---|---|---|---|
| 2007/0273357 A1* | 11/2007 | Saito et al. | 324/71.5 |
| 2008/0084564 A1* | 4/2008 | He et al. | 356/456 |
| 2009/0134329 A1* | 5/2009 | Kasai et al. | 250/338.1 |

FOREIGN PATENT DOCUMENTS

| | | |
|---|---|---|
| JP | 2004-125712 | 4/2004 |
| JP | 2005-315708 | 11/2005 |
| JP | 2007-503582 | 2/2007 |
| JP | 2007-298357 | 11/2007 |
| WO | 2006/030756 | 3/2006 |

OTHER PUBLICATIONS

Charles Kittel, "Introduction to Solid State Physics", vol. 1, 7th Edition, translated by Ryousei Uno, Noboru Tsuya, Akira Morita, and Jiro Yamashita (published by Maruzen Company, Limisted, 1998), pp. 321-328.

Usami et al., "Characterization of epitaxial semiconductor layers using terahertz time-domain spetroscopy", Bunseki Kagaku, vol. 52, No. 6, pp. 455-460, (Jun. 5, 2003).

Jeon T I, et al., "Characterization of Optically Dence, Doped Semiconductors by Reflection THz Time Domain Spectroscopy", Applied Physics Letters, vol. 72, No. 23, pp. 3032-30349, (Jun. 8, 1998).

Holm R T, et al., "Infrared Reflectance Studies of Bulk and Epitaxial-Film n-type GaAs", Journal of Applied Physics, vol. 48, No. 1, pp. 212-223, (1977).

Kikuchi, et al., "Measurement of Intensity Distribution of THz Waves in a DAST Crystal Pumped with a Diode Laser", The Japan Society of Applied Physics, Dai 65 kai, separate vol. 3, p. 976 2p-ZD-1, (Sep. 1, 2004).

Ono, et al., "The First Stage of Real-Time Reflective Imaging Using a DAST-DFG ", The Japan Society of Applied Physics, Dai 69 kai, separate vol. 3, p. 988 5a-ZE-7, (Sep. 2, 2008).

International Search Report Dated Mar. 17, 2009.

* cited by examiner

CARRIER CONCENTRATION MEASURING DEVICE AND CARRIER CONCENTRATION MEASURING METHOD

TECHNICAL FIELD

The present invention relates to a carrier concentration measuring device and a method for measuring the carrier concentration of an impurity-doped inorganic compound semiconductor.

BACKGROUND ART

It is known that an inorganic compound has high-reflection properties, as the permittivity of the inorganic compound has a negative value in a band between TO phonon frequency (transverse optical phonon frequency) and LO phonon frequency (longitudinal optical phonon frequency) (see Non-Patent Literatures 1 and 2).

Patent Literature 1 discloses a method for determining a carrier concentration with a terahertz light reflection measuring device. By this method, a magnetic field is applied while terahertz light is being irradiated to the material to be measured. A hole coefficient is measured by observing an electric field generated by a hole effect, and a carrier concentration is determined. Also, by this method, a terahertz wave generating device that uses a femtosecond laser is used as the terahertz light source. In this terahertz wave generating device, the response time of the generated electric field is several picoseconds, and terahertz light of 0.5 to 2.0 THz in frequency is oscillated.

Patent Literature 2 discloses a method for inspecting the property information about a semiconductor material through transmittance measurement using terahertz light. By this method, transmission measurement is carried out, and the property information is identified based on absorption loss of the semiconductor.

[Patent Literature 1] Japanese Patent Application Laid-Open No. 2005-315708
[Patent Literature 2] Japanese Patent Application Laid-Open No. 2002-5828
[Non-Patent Literature 1] K. A. Maslin, C. Patel and T. J. Parker, "Far-Infrared Optical Constants of a Selection of Zincblende Structure Crystals at 300 K", Infrared Physics, Vol. 32 (1991), P. 303-310
[Non-Patent Literature 2] Charles. Kittel, "Introduction to Solid State Physics", Vol. 1, 7th Edition, translated by Ryousei Uno, Noboru Tsuya, Akira Morita, and Jiro Yamashita (published by Maruzen Company, Limited, 1998), P. 321-328

DISCLOSURE OF THE INVENTION

However, the conventional techniques disclosed in the above literatures have more room for improvement.

By the method disclosed in Patent Literature 1, a mechanism for applying a magnetic field as well as terahertz waves needs to be prepared. As a result, the device becomes costly and large in size. Also, a special circuit is required to capture an electric field of a few picoseconds. Further, the frequency to be oscillated by terahertz waves is limited to the range of 0.5 to 2 THz.

By the transmittance measurement disclosed in Patent Literature 2, information containing both reflection loss and absorption loss is obtained. Therefore, it is necessary to estimate reflection loss, and the procedures to calculate the property information become complicated. FIG. 12 shows the results of measurement of the transmittance and reflectance of gallium nitride (GaN). In the graph shown in FIG. 12, the abscissa axis indicates the frequency [THz], the left ordinate axis indicates the transmittance, and the right ordinate axis indicates the reflectance. As shown in FIG. 12, while the transmittance data varies within the range of 0 to 0.2, the reflectance data varies from 0 to 1. Therefore, to measure absorption loss, it is necessary to measure both the transmittance and the reflectance. Furthermore, to measure absorption loss, it is also necessary to prepare samples that have uniform thicknesses and uniform surface states. As a result, a destructive inspection is carried out.

To solve the above problems, the present invention aims to readily measure the carrier concentration of an inorganic compound semiconductor in a nondestructive manner.

According to the present invention, there is provided a carrier concentration measuring device that measures a carrier concentration of an impurity-doped inorganic compound semiconductor, comprising: a storage unit that stores a correlation between the reflectance of the inorganic compound semiconductor against terahertz light and the carrier concentration; a light radiation unit that irradiates the terahertz light to the inorganic compound semiconductor as a sample; a detection unit that detects reflected light of the inorganic compound semiconductor against the irradiated terahertz light; a reflectance calculation unit that calculates an actual measurement value of the reflectance of the inorganic compound semiconductor by determining a ratio of intensity of the reflected light to intensity of the irradiated terahertz light; and a read unit that refers to the stored correlation and reads the carrier concentration of the sample corresponding to the actual measurement value of the reflectance.

According to the present invention, there is provided a carrier concentration measuring method for measuring the carrier concentration of an impurity-doped inorganic compound semiconductor, comprising: acquiring a correlation between the reflectance of the inorganic compound semiconductor against terahertz light and the carrier concentration; irradiating the terahertz light to the inorganic compound semiconductor as a sample; detecting reflected light of the inorganic compound semiconductor against the irradiated terahertz light; calculating an actual measurement value of the reflectance of the inorganic compound semiconductor by determining a ratio of intensity of the reflected light to intensity of the irradiated terahertz light; and reading the carrier concentration of the sample corresponding to the actual measurement value of the reflectance calculated, by referring to the stored correlation.

According to the present invention, the correlation between the reflectance of an inorganic compound semiconductor against terahertz light and a carrier concentration is stored. The carrier concentration of a sample corresponding to the actual measurement value of the reflectance of the inorganic compound semiconductor against the terahertz light is read by referring to the stored correlation. In this manner, the carrier concentration of the sample can be determined by simply measuring the reflectance against terahertz light, without any processing of the sample as a preparation. Accordingly, the carrier concentration of the inorganic compound semiconductor can be readily measured in a nondestructive manner.

The components according to the present invention are not necessarily independent of one another. Two or more components may be formed as a single member, a single component may be formed with two or more members, a component may be part of another component, part of a component overlaps with part of another component, or the like.

The procedures of a carrier concentration measuring device according to the present invention are described in order. However, the order disclosed in this specification does not restrict the order of procedures to be carried out. Therefore, when the carrier concentration measuring method according to the present invention is implemented, the order of procedures to be carried out may be changed unless any inconvenience is caused.

Further, the procedures in the carrier concentration measuring method according to the present invention are not necessarily carried out in different timings. A procedure may be carried out while another procedure is being carried out, the timing for a procedure may partially or perfectly overlaps with the timing for another procedure, or the like.

According to the present invention, the carrier concentration of an inorganic compound semiconductor can be easily measured in a nondestructive manner.

BRIEF DESCRIPTION OF THE DRAWINGS

The above mentioned objects and other objects, and features and advantages of the present invention will become more apparent from the following detailed description when read in conjunction with the accompanying drawings.

BEST MODE FOR CARRYING OUT THE INVENTION

Figure 1:
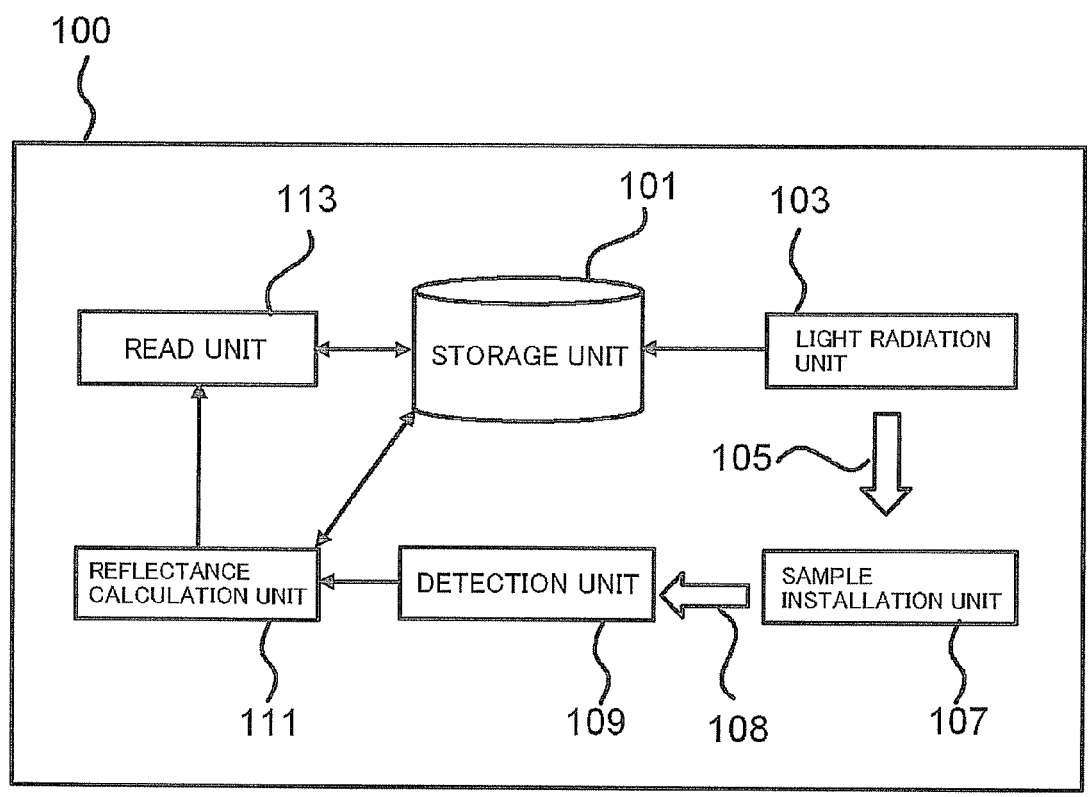
FIG. 1 is a block diagram schematically showing a nondestructive carrier concentration measuring device according to an embodiment of the present invention.

The following is a detailed description of an embodiment of the present invention, with reference to the accompanying drawings. Like components are denoted by like reference numerals in all the drawings, and description of those components is not repeated.

This embodiment provides a carrier concentration measuring device that measures the carrier concentration of an impurity-doped inorganic compound semiconductor. FIG. 1 is a block diagram schematically showing the nondestructive carrier concentration measuring device 100 of this embodiment.

The nondestructive carrier concentration measuring device 100 of this embodiment includes: a storage unit 101 that stores the correlation between the reflectance of an inorganic compound semiconductor against terahertz light and a carrier concentration; a light radiation unit 103 that irradiates the terahertz light 105 to the inorganic compound semiconductor as a sample; a detection unit 109 that detects reflected light 108 of the inorganic compound semiconductor against the irradiated terahertz light 105; a reflectance calculation unit 111 that calculates an actual measurement value of the reflectance of the inorganic compound semiconductor based on the irradiated terahertz light 105 and the reflected light 108; and a read unit 113 that refers to the stored correlation and reads the carrier concentration of the sample corresponding to the actual measurement value of the reflectance.

The nondestructive carrier concentration measuring device 100 also includes a sample mounting unit 107. The sample mounting unit 107 installs the organic compound semiconductor as a sample.

Examples of materials that may be used for the organic compound semiconductor include gallium nitride (GaN), silicon carbide (SiC), gallium arsenide (GaAs), aluminum gallium nitride (GaAlN), GaP, GaSb, InN, InP, InAs, InSb, AlN, AlP, AlAs, AlSb, ZnS, ZnSe, ZnTe, CdS, CdSe, CdTe, AlGaP, AlGaAs, AlGaSb, GaInN, GaInP, GaInAs, GaInSb, AlInN, AlInP, AlInAs, and AlInSb.

The impurities (added materials) with which the inorganic compound semiconductor is doped may be silicon, nitrogen, or phosphorus of an n-type (a donor), for example.

The correlation between the reflectance and the carrier concentration stored in the storage unit 101 is expressed by the following formulae (1) through (4) with the use of permittivity. Table 1 shows each parameter. The reflectance can be calculated according to the following formulae (1) through (4). The formulae are cited from Non-Patent Literature 3. The free electron plasma frequency $\omega_p$ is determined according to the formula (2), which involves the carrier concentration N. The plasma frequency $\omega_p$ obtained by is substituted into the formula (1), to determine the permittivity $\epsilon$. The determined permittivity $\epsilon$ is expressed by the formula (3), where the real part of the square root of the permittivity ($\sqrt{\epsilon}$) is the refractive index n, and the imaginary part of the square root of the permittivity is the extinction coefficient $\kappa$. The reflectance R is determined according to the formula (4) with the use of the refractive index n and the extinction coefficient $\kappa$. Therefore, when the carrier concentration N varies, the reflectance R also varies.

[Formula 1]

$$\varepsilon = \varepsilon_\infty \left( 1 + \frac{\omega_L^2 - \omega_T^2}{\omega_T^2 - \omega^2 + i\omega\Gamma} - \frac{\omega_p^2}{\omega(\omega - i\gamma)} \right) \quad (1)$$

[Formula 2]

$$\omega_p = \frac{4\pi N e^2}{m^* \varepsilon_\infty} \quad (2)$$

[Formula 3]

$$\varepsilon = (n - i\kappa)^2 \quad (3)$$

[Formula 4]

$$R = \frac{(n-1)^2 + \kappa^2}{(n+1)^2 + \kappa^2} \quad (4)$$

TABLE 1

| PARAMETER | | UNIT |
|---|---|---|
| $\omega$ | FREQUENCY | [cm$^{-1}$] |
| $\epsilon$ | PERMITTIVITY | |
| $\omega_L$ | LO PHONON FREQUENCY | [cm$^{-1}$] |
| $\omega_T$ | TO PHONON FREQUENCY | [cm$^{-1}$] |
| $\Gamma$ | PHONON DAMPING FACTOR | |
| $\omega_P$ | FREE ELECTRON PLASMA FREQUENCY | [cm$^{-1}$] |
| $\gamma$ | FREE ELECTRON DAMPING FACTOR | |
| $\epsilon_\infty$ | PERMITTIVITY AT REASONABLY HIGH FREQUENCY | |
| N | CARRIER CONCENTRATION | [atoms/cm$^3$] |
| e | CHARGE | [C] |
| m* | ELECTRON EFFECTIVE MASS | [g] |
| n | REFRACTIVE INDEX | |
| $\kappa$ | EXTINCTION COEFFICIENT | |
| R | REFLECTANCE | |

(Non-Patent Literature 3) R. T. Holm, J. W. Gibson and E. D. Palik, "Infrared reflectance studies of bulk and epitaxial-film n-type GaAs", Journal of Applied Physics, Vol. (1977), P. 212-223

As described above, the reflectance representing the correlation is determined according to the formulae (1) through (4) in the following manner. The permittivity of the inorganic compound semiconductor is calculated from the carrier concentration, and a predicted reflectance is calculated form the calculated permittivity. The correlation between the calculated predicted reflectance and the carrier concentration is then determined. The correlation between the predicted reflectance and the carrier concentration is stored into the storage unit 101.

The light radiation unit 103 applies a second harmonic (532 nm in wavelength) of a Nd:YAG laser onto an optical parametric oscillator that uses KTP crystals, to oscillate two wavelengths in a 1.3 μm band. The two wavelengths are applied to DAST crystals (4-dimethylamino-N-methyl-4-stilabazolium-tosylate), to irradiate light waves of 1.5 to 40 terahertz band. If terahertz light can be irradiated to the inorganic compound semiconductor as a sample, some other crystals may be used, instead of DAST crystals. Also, light waves of a terahertz band oscillated with a femtosecond laser may be used. The light radiation unit 103 stores information such as the wavelength and light intensity of the irradiated light, and the incident angle with respect to the sample, into the storage unit 101.

The detection unit 109 sends the incident angle of detected reflected light to the reflectance calculation unit 111. A DTGS (Deuterated Triglycine Sulfate) detector may be used as the detection unit 109.

The reflectance calculation unit 111 receives, from the detection unit 109, the information such as the incident angle and light intensity of the reflected light detected by the detection unit 109. The reflectance calculation unit 111 then calculates an actual measurement value of the reflectance, based on the information about the irradiated light stored in the storage unit 101 and the information about the reflected light. The calculated reflectance is sent to the read unit 113. Alternatively, the calculated reflectance may be stored into the storage unit 101, or may be output.

The reflectance can be measured in the following manner. First, a reference plate (a gold mirror, for example) is placed on the sample mounting unit 107. The light reflected by the gold mirror receiving irradiated light is defined as an irradiated light intensity. A compound semiconductor is then placed on the sample mounting unit 107. The light reflected by the compound semiconductor receiving irradiated light is defined as a reflected light intensity. The value obtained by dividing the irradiated light intensity by the reflected light intensity is measured as the reflectance.

The read unit 113 refers to the storage unit 101. Based on the stored correlation, the read unit 113 obtains the carrier concentration from the reflectance received from the reflectance calculation unit 111. The read unit 113 can output the obtained carrier concentration.

Also, according to the formulae (1) through (4), the reflectance (measured reflectance) against terahertz light in a measurement band in which the reflectance of an inorganic compound semiconductor against terahertz light varies depending on the carrier concentration is determined. Also, the reflectance (reference reflectance) against terahertz light in a reference band in which the reflectance of the inorganic compound semiconductor against terahertz light does not vary depending on the carrier concentration is determined. Accordingly, a predicted reflectance ratio between the measured reflectance and the reference reflectance can be calculated. The correlation between the predicted reflectance ratio and the carrier concentration can be stored into the storage unit 101.

The light radiation unit 103 irradiates the terahertz light of the measurement band and the terahertz light of the reference band onto the sample. The reflectance calculation unit 111 compares the reflectance calculated when the terahertz light of the measurement band is irradiated with the reflectance calculated when the terahertz light of the reference band is irradiated. In this manner, the reflectance calculation unit 111 calculates the actual measurement value of the reflectance ratio. The read unit 113 refers to the correlation between the reflectance ratio and the carrier concentration stored in the storage unit 101. In this manner, the read unit 113 can read the carrier concentration corresponding to the actual measurement value of the reflectance ratio.

The reference band may be a high-reflection band between TO phonon frequency and LO phonon frequency.

In the following, the structure of the nondestructive carrier concentration measuring device according to this embodiment is described in greater detail, with reference to the accompanying drawings.

Figure 2:
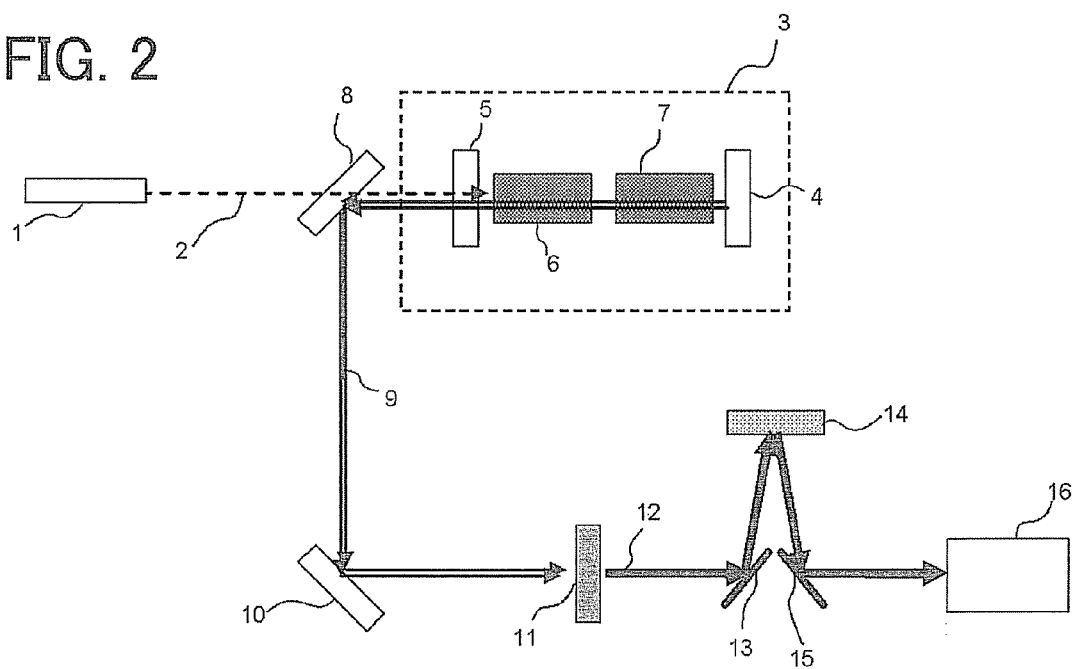
FIG. 2 illustrates an example structure of the nondestructive carrier concentration measuring device according to one embodiment of the present invention.

FIG. 2 shows an example structure of the nondestructive carrier concentration measuring device. As a terahertz light oscillating device, an optical parametric oscillator 3 that uses DAST crystals 11 according to Non-Patent Literature 4 is used. The second harmonic (532 nm in wavelength) of a Nd:YAG laser 1 is used as excitation light 2 of the optical parametric oscillator 3. The excitation light 2 is applied to the optical parametric oscillator 3. In the optical parametric oscillator 3, two KTP crystals (KTiOPO$_4$ crystals) that have crystal angles slightly different from each other are placed in a resonator formed with a reflecting mirror 4 and a transmitting mirror 5. The KTP crystal 6 and the KTP crystal 7 can oscillate two different wavelengths 9 of a 1.3 μm band. The two wavelengths 9 of the 1.3 μm band are reflected by a reflecting mirror 8 and a reflecting mirror 10. As the reflected wavelengths enters a DAST crystal 11, terahertz light 12 (a terahertz wave) of equal to or more than 1.5 THz and equal to and less than 47 THz can be extracted by virtue of a nonlinear optical effect. The oscillated terahertz light 12 is reflected by a reflecting mirror 13, and is irradiated to an inorganic compound semiconductor 14. The terahertz light 12 reflected by the inorganic compound semiconductor 14 is further reflected by a reflecting mirror 15, and is received by a DTGS detector 16.

(Non-Patent Literature 4) H. Ito, K. Suizu, T. Yamashita, A. Nawahara and T. Sato, "Random Frequency Accessible Broad Tunable Terahertz-Wave Source Using Phase-Matched 4-Dimethylamino-N-Methyl-4-stilbazolium Tosylate Crystal," Japanese Journal Applied Physics, Vol. 46 (2007), P. 7321-7324

Figure 3:
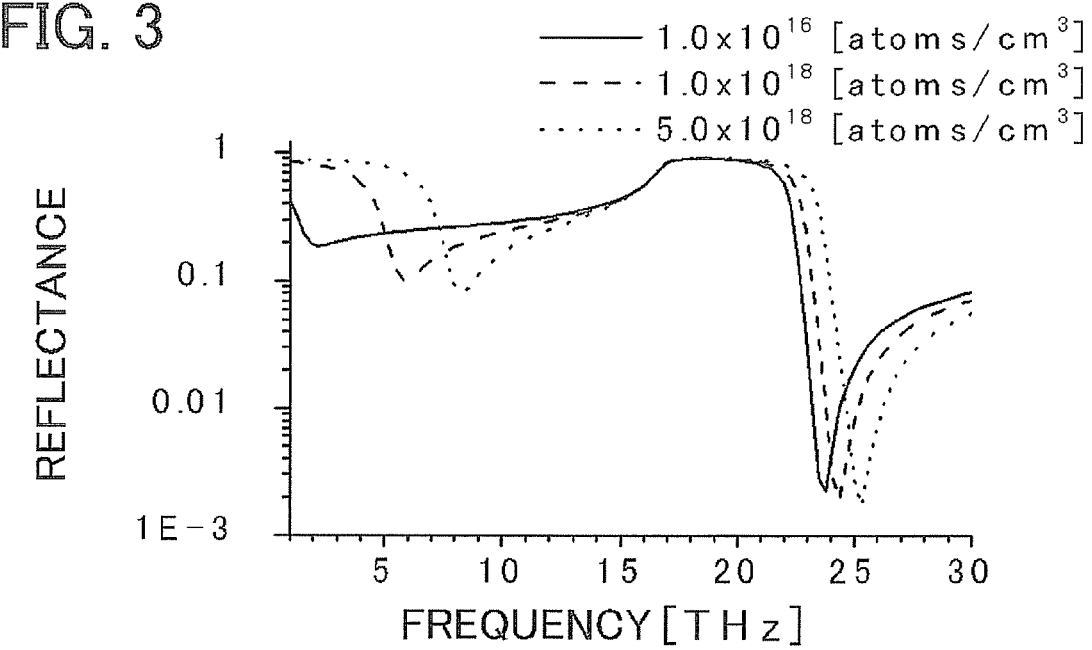
FIG. 3 shows the relation of calculated reflectance of GaN to frequency.
Figure 4:
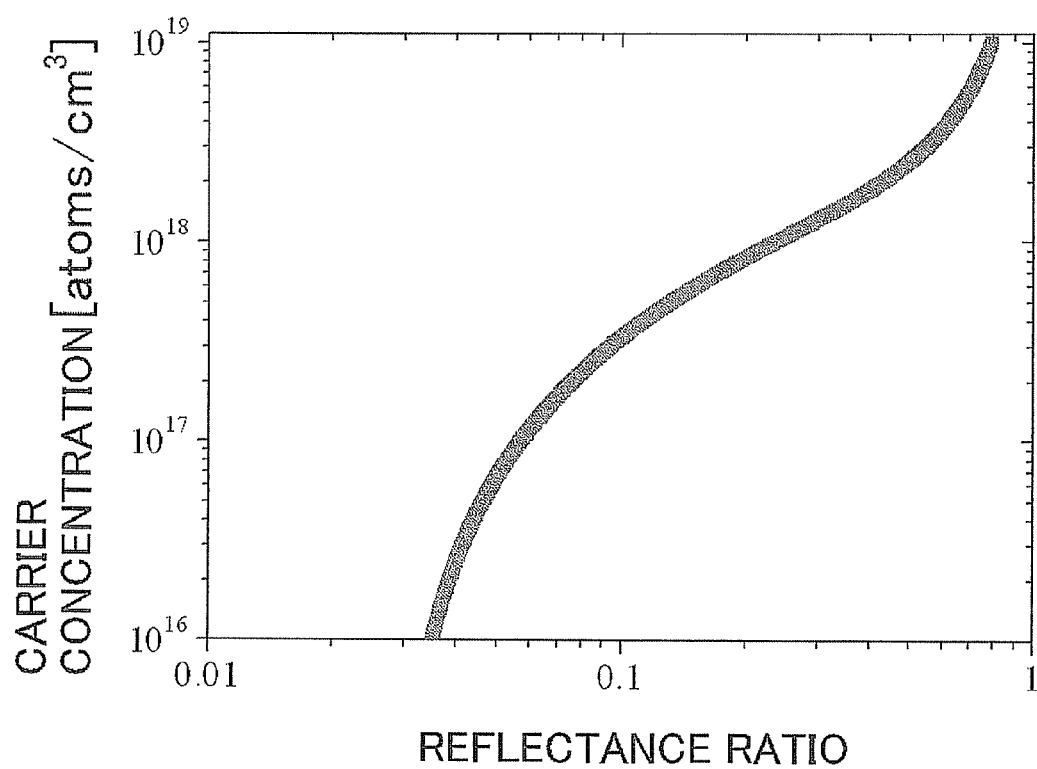
FIG. 4 shows the relation between the calculated reflectance of GaN and the carrier concentration.

A method for measuring a carrier concentration of GaN with the use of the device illustrated in FIG. 1 is now described. First, the correlation between the reflectance of an inorganic compound semiconductor against terahertz light and the carrier concentration is determined according to the formulae (1) through (4). FIG. 3 shows the relation of the reflectance to the calculated GaN frequency. In the graph shown in FIG. 3, the abscissa axis indicates the frequency [THz], and the ordinate axis indicates the reflectance. The results of calculations performed on GaN having a carrier concentration of $1.0 \times 10^{16}$ [atoms/cm$^3$] and GaN having a carrier concentration of $1.0 \times 10^{18}$ [atoms/cm$^3$] are shown in the graph of FIG. 3. Total reflection is observed in the frequency band of equal to or more than 17 THz and equal to or less than 20 THz, regardless of fluctuations of carrier concentrations. The reflectance varies with changes in carrier concentration in the frequency band of equal to or more than 1 THz and equal to or less than 16 THz. The reflectance also varies with changes in carrier concentration in the frequency band of equal to or more than 21 THz and equal to or less than 23 THz. Therefore, the band of equal to or more than 17 THz and equal to or less than 20 THz can be set as the reference band, and the band of equal to or more than 1 THz and equal to or less than 16 THz or the band of equal to or more than 21 THz and equal to or less than 23 THz can be set as the measurement band. FIG. 4 shows the relationship between the GaN reflectance determined through the calculation and the carrier concentration.

In the graph shown in FIG. 4, the abscissa axis indicates the carrier concentration [atoms/cm$^3$] and the ordinate axis indicates the reflectance. More specifically, the reflectance shown in FIG. 4 indicates the reflectance against terahertz light of other bands, with the reflectance against terahertz light of the reference band being "1". In other words, the reflectance shown in FIG. 4 indicates a predicted reflectance ratio according to this embodiment. The storage unit 101 stores data indicating the correlation shown in FIG. 4.

A sample of GaN having an unknown carrier concentration is prepared, and is placed on the sample mounting unit 107. The light radiation unit 103 irradiates two light waves to the sample. The two light waves are a light wave of terahertz light of a high-reflection band as the reference band of equal to or more than 17 THz and equal to or less than 20 THz, and a light wave of terahertz light of the measurement band of equal to or more than 1 THz and equal to or less than 16 THz or equal to or more than 21 THz and equal to or less than 23 THz in which the reflectance varies with the carrier concentration.

The detection unit 109 detects the light reflected by the sample receiving the irradiated terahertz light of the reference band. The detection unit 109 also detects the light reflected by the sample receiving the irradiated terahertz light of the measurement band.

The reflectance calculation unit 111 compares the detected reflected light with the irradiated terahertz light of the reference band, to calculate the reference reflectance. The reflectance calculation unit 111 also compares the detected reflected light with the irradiated terahertz light of the measurement band, to calculate the measured reflectance. The reflectance calculation unit 111 then compares the measured reflectance with the reference reflectance, to calculate an actual measurement value of the reflectance.

The read unit 113 refers to the correlation chart of FIG. 4 stored in the storage unit 101, and reads the carrier concentration of the sample corresponding to the calculated actual measurement value of the reflectance from the ordinate axis. In this manner, the carrier concentration of the sample can be measured.

The advantages of this embodiment are now described. According to this embodiment, the correlation between the reflectance of an inorganic compound semiconductor against terahertz light and the carrier concentration is stored, and the carrier concentration of a sample corresponding to the actual measurement value of the reflectance of the inorganic compound semiconductor against the terahertz light is read by referring to the stored correlation. With this arrangement, the sample does not need to be processed in the preparation stage, and the carrier concentration of the sample can be measured simply by measuring the reflectance against terahertz light. Accordingly, the carrier concentration of an inorganic compound semiconductor can be readily measured in a nondestructive manner.

As a result of intensive studies, the inventors discovered that there is a correlation between the reflectance of a terahertz wave and a carrier concentration in an impurity-doped inorganic compound semiconductor, and the carrier concentration can be calculated with two light waves. Accordingly, the carrier concentration of an inorganic compound semiconductor can be measured in a nondestructive manner.

In the carrier concentration measuring device of this embodiment, free electrons serving as active ions are regarded as carriers for the purpose of calculation. Free electrons are defined as carriers, and the carrier concentration can be determined through a calculation. The carrier concentration determined through a calculation matches the results of secondary ion mass spectroscopy (SIMS) and hole measurement. Accordingly, by using the device of this embodiment, the carrier concentration of an inorganic compound semiconductor can be readily measured in a nondestructive manner.

By the nondestructive carrier concentration measuring method using the device of this embodiment, the reflectance is measured by the two light waves to GaN as a sample. The two light waves are a light wave of terahertz light of a high-reflection band as the reference band of equal to or more than 17 and equal to or less than 20 THz, and a light wave of terahertz light of the measurement band of equal to or more than 1 THz and equal to or less than 16 THz or equal to or more than 21 THz and equal to or less than 23 THz in which the reflectance varies with the carrier concentration. By this method, the reflectance of the inorganic compound semiconductor against the terahertz light of one of the two light waves is compared with the reflectance of the inorganic compound semiconductor against the terahertz light of the other one of the two light waves, and the correlation between the obtained reflectance ratio and the carrier concentration is obtained in advance. The carrier concentration of the sample according to the actually measured reflectance ratio is read. Accordingly, the carrier concentration of an inorganic compound semiconductor can be measured in a short period of time in a nondestructive manner.

In hole measurement, for example, solder is warmed, and an electrode is attached. Four terminals are then positioned to the electrode, and contact measurement is carried out. To attach an electrode, the inorganic compound semiconductor handled as a sample needs to be processed into a flat form. If the sample is used as a product after the measurement, the electrode needs to be removed, and reprocessing needs to be performed.

With the carrier concentration measuring device of this embodiment, on the other hand, a sample is placed on a wafer holder, and is simply measured. Also, the sample does not need to be processed into a flat form as in the hole measurement, and measurement can be carried out in an as-grown state. Accordingly, the process time required for the preparation is unnecessary. The carrier concentration can be measured only with the use of two kinds of terahertz light. The measurement time is estimated to be a few seconds to several tens of seconds. Accordingly, with this device, the carrier concentration can be measured in a short period of time. Also, since the measurement is carried out in a nondestructive manner, the sample can be shipped as a product after the measurement.

Although an embodiment of the present invention has been described with reference to the accompanying drawings, this is merely an example, and various other structures may be employed.

The following are examples of the other structures.

(1) A method for measuring the carrier concentration of an inorganic compound semiconductor, the method including: irradiating terahertz light of two wavelengths to the inorganic compound semiconductor, with the terahertz light of two wavelengths being terahertz light of a reference band in which the reflectance does not depend on the carrier concentration and is constant, and terahertz light of a measurement band in which the reflectance varies with the carrier concentration; and comparing the reflectance of one of the two light waves with the reflectance of the other one of the two light waves, to measure the carrier concentration of the inorganic compound semiconductor.

(2) The method according to (1), wherein the reference band is a high-reflection band between TO phonon frequency and LO phonon frequency.

(3) The method according to (1) or (2), wherein the inorganic compound semiconductor is gallium nitride (GaN), the reference band is a band of 17 to 20 THz, and the measurement band is a band of 1 to 16 THz or 21 to 23 THz.

(4) The method according to (1) or (2), wherein the inorganic compound semiconductor is silicon carbide (SiC), the reference band to be used is a band of 25 to 27 THz, and the measurement band is a band of 28 to 30 THz.

(5) The method according to (1) or (2), wherein the inorganic compound semiconductor is gallium arsenide (GaAs), the reference band to be used is a band of 8.2 to 8.5 THz, and the measurement band is a band of 8.6 to 8.8 THz.

(6) A device for measuring the carrier concentration of an inorganic compound semiconductor, the device including: irradiating terahertz light of two wavelengths to the inorganic compound semiconductor, with the terahertz light of two wavelengths being terahertz light of a reference band in which the reflectance does not depend on the carrier concentration and is constant, and terahertz light of a measurement band in which the reflectance varies depending on the carrier concentration; and comparing the reflectance of one of the two light waves with the reflectance of the other one of the two light waves, to measure the carrier concentration of the inorganic compound semiconductor.

(7) The device according to (6), which is characterized by using DAST crystals as the crystals for generating light waves of terahertz bands.

According to the above aspects, the carrier concentration of an inorganic compound semiconductor can be calculated in a short period of time in a nondestructive manner by: irradiating terahertz light of two wavelengths to the inorganic compound semiconductor, with the terahertz light of two wavelengths being terahertz light of a reference band in which the reflectance does not depend on the carrier concentration and is constant, and terahertz light of a measurement band in which the reflectance varies depending on the carrier concentration; and comparing the reflectance of one of the two light waves with the reflectance of the other one of the two light waves.

According to the present invention, the carrier concentration of GaP, GaSb, InN, InP, InAs, InSb, AlN, Alp, AlAs, AlSb, ZnS, ZnSe, ZnTe, CdS, CdSe, or CdTe can also be calculated by: irradiating terahertz light of two wavelengths to the inorganic compound semiconductor, with the terahertz light of two wavelengths being terahertz light of a reference band in which the reflectance does not depend on the carrier concentration and is constant, and terahertz light of a measurement band in which the reflectance varies depending on the carrier concentration; and comparing the reflectance of one of the two light waves with the reflectance of the other one of the two light waves.

According to the present invention, the carrier concentration of AlGaP, AlGaAs, AlGaSb, GaInN, GaInP, GaInAs, GaInSb, AlInN, AlInP, AlInAs, or AlInSb can also be calculated by: irradiating terahertz light of two wavelengths to the inorganic compound semiconductor, with the terahertz light of two wavelengths being terahertz light of a reference band in which the reflectance does not depend on the carrier concentration and is constant, and terahertz light of a measurement band in which the reflectance varies depending on the carrier concentration; and comparing the reflectance of one of the two light waves with the reflectance of the other one of the two light waves.

It is of course possible to combine the above described embodiments unless the combined embodiments are incompatible with each other. Although the structure of each components of the above embodiments has been described in detail, various modifications may be made to those structures within the scope of the invention.

EXAMPLES

Example 1

The carrier concentration of GaN was measured with the use of the carrier concentration measuring device illustrated in FIG. 2. The carrier concentration of GaN as an inorganic compound semiconductor was measured. The shape of each used sample in a plan view is equal to or more than 10 mm square and equal to or less than 15 mm square having a thickness of equal to or more than 1.0 mm to and equal to or less than 2.0 mm. The used samples have carrier concentrations of $2.7 \times 10^{16}$ [atoms/cm$^3$], $1.2 \times 10^{18}$ [atoms/cm$^3$], and $2.2 \times 10^{18}$ [atoms/cm$^3$] measured by secondary ion mass spectroscopy (SIMS). The samples are as-grown crystals that do not have processing and polishing performed on their measurement faces.

Figure 5:
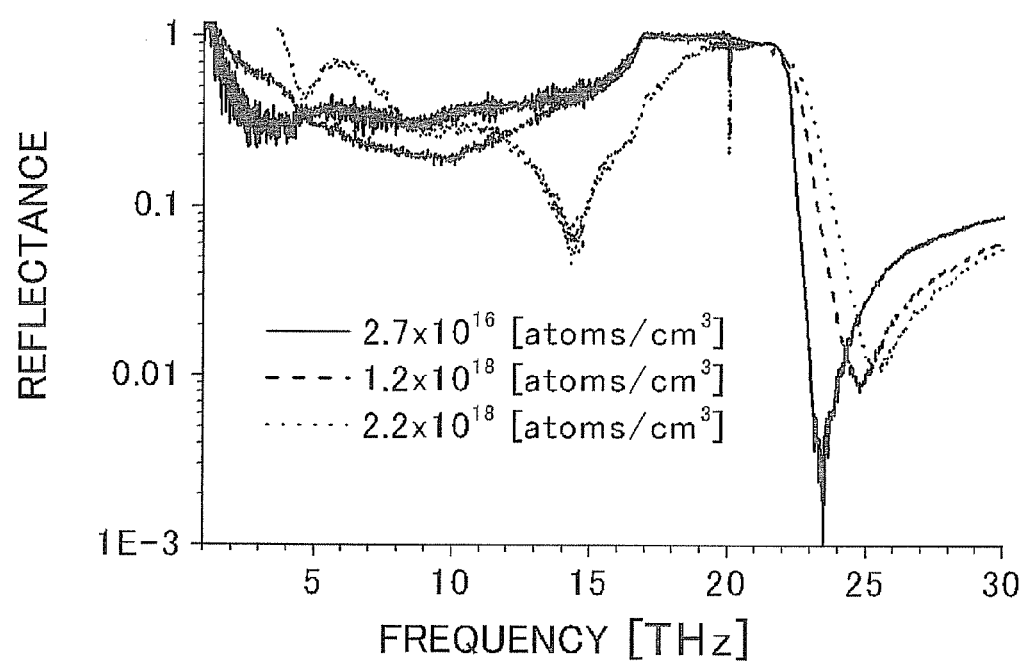
FIG. 5 shows the results of measurement of the reflectance of GaN to frequency.

FIG. 5 shows the results of measurement of the reflectance of GaN against frequency. In the graph shown in FIG. 5, the abscissa axis indicates the frequency [THz], and the ordinate axis indicates the reflectance. The results of measurement carried out on GaN having the carrier concentrations of $2.7 \times 10^{16}$, $1.2 \times 10^{18}$, and $2.2 \times 10^{18}$ [atoms/cm$^3$] are shown in the graph of FIG. 5. The reflectance varies with changes in carrier concentration in equal to or more than 1 THz and equal to or less than 16 THz. High reflection is observed in equal to or more than 17 THz and equal to or less than 20 THz. The reflectance also varies with changes in carrier concentration in equal to or more than 21 THz and equal to or less than 23 THz. Therefore, the measurement band was set equal to or more than 1 THz and equal to or less than 16 THz or equal to or more than 21 THz and equal to or less than 23 THz, and the reference band was set equal to or more than 17 THz and equal to or less than 20 THz.

Figure 6:
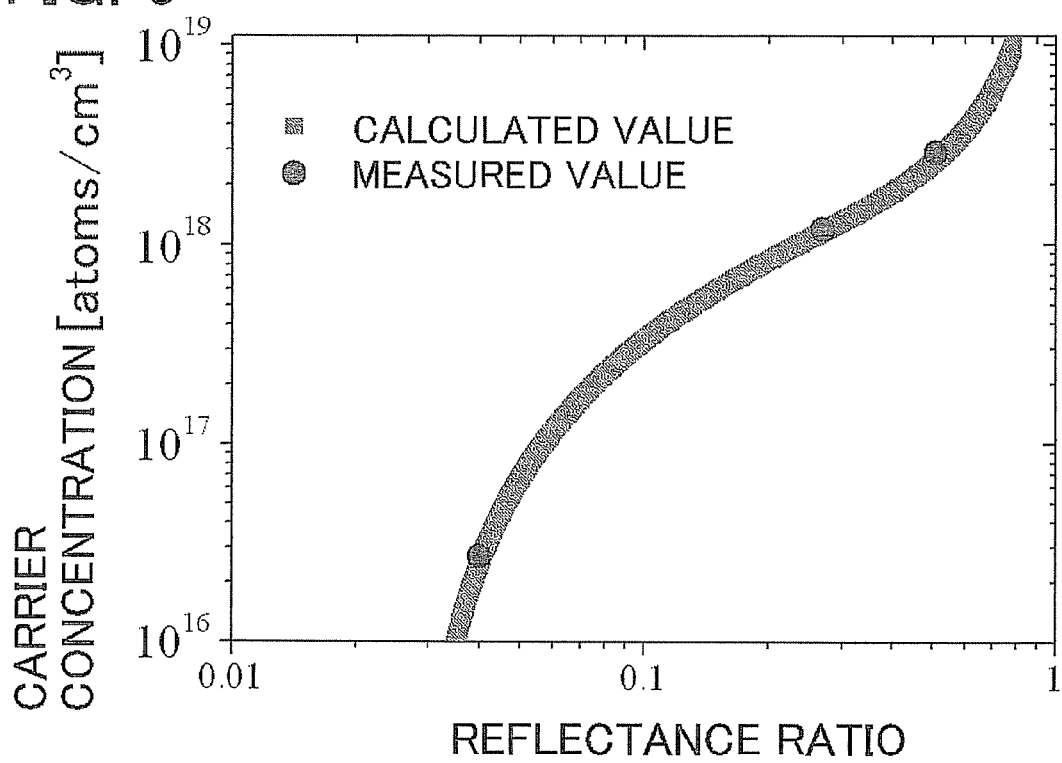
FIG. 6 shows the calculated values and the measured values of the reflectance and the carrier concentration of GaN.

FIG. 6 shows the calculated values and the measured values of the reflectance ratio and the carrier concentration of GaN. In the graph shown in FIG. 6, the abscissa axis indicates the reflectance ratio, and the ordinate axis indicates the carrier concentration [atoms/cm$^3$]. FIG. 6 shows the calculated values of the carrier concentration with respect to the reflectance ratios that are determined by comparing the reflectance of a light wave of a terahertz wave from a high-reflection band (the reference band) with the reflectance of a light wave of terahertz light from a band (the measurement band) in which the reflectance varies with the carrier concentration, and the SIMS measured values. As can be seen from FIG. 6, the carrier concentration determined from the measured reflectance is the same as the carrier concentration determined by SIMS measurement. This proves that the carrier concentration can be calculated only with the use of terahertz light of two wavelengths.

Example 2

The carrier concentration of SiC (silicon carbide) was measured with the use of the carrier concentration measuring device illustrated in FIG. 2. The shape of each used sample in a plan view is equal to or more than 10 mm square and equal to or less than 15 mm square having a thickness of equal to or more than 0.2 mm and equal to or less than 0.7 mm. The used samples are as-grown crystals that have carrier concentrations of $2.7 \times 10^{17}$ [atoms/cm$^3$] and $4.2 \times 10^{18}$ [atoms/cm$^3$].

Figure 7:
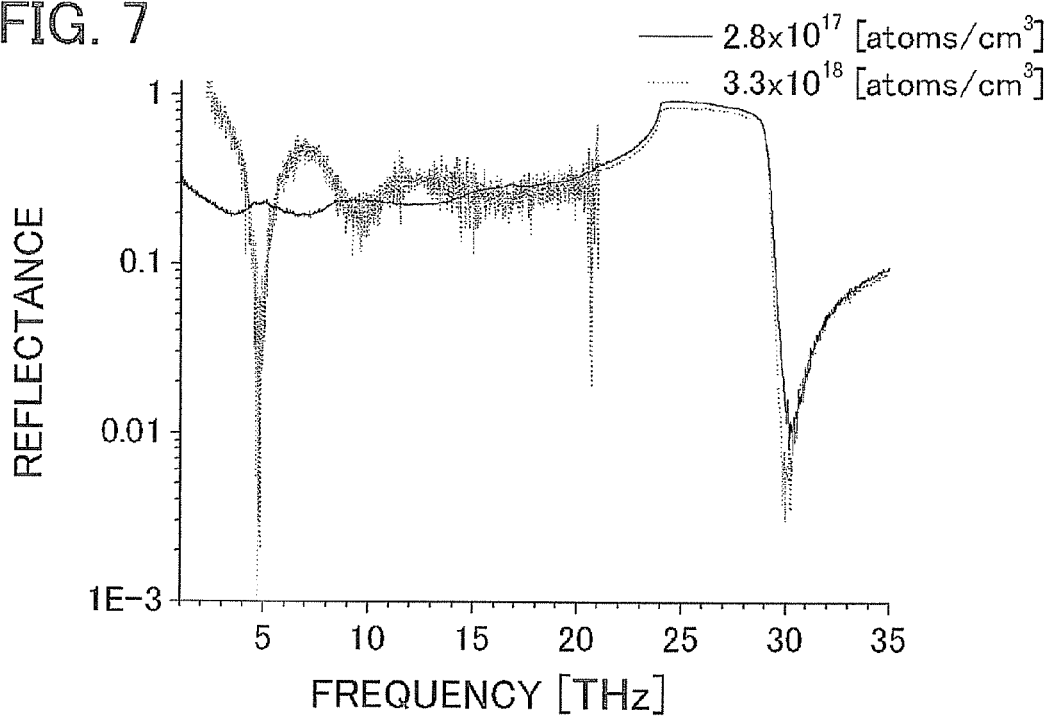
FIG. 7 shows the results of measurement of the reflectance of SiC to frequency.

FIG. 7 shows the results of measurement of the reflectance of SiC against frequency. In the graph shown in FIG. 7, the abscissa axis indicates the frequency [THz], and the ordinate axis indicates the reflectance. The results of measurement carried out on SiC having the carrier concentrations of $2.8 \times 10^{17}$ and $3.3 \times 10^{18}$ [atoms/cm$^3$] are shown in the graph of FIG. 7. High reflection is observed in equal to or more than 25 THz and equal to or less than 27 THz. The reflectance varies with changes in carrier concentration in equal to or more than 1 THz and equal to or less than 24 THz and equal to or more than 28 THz and equal to or less than 30 THz. Therefore, the measurement band was set equal to or more than 28 THz and equal to or less than 30 THz, and the reference band was set equal to or more than 25 THz and equal to or less than 27 THz.

Figure 8:
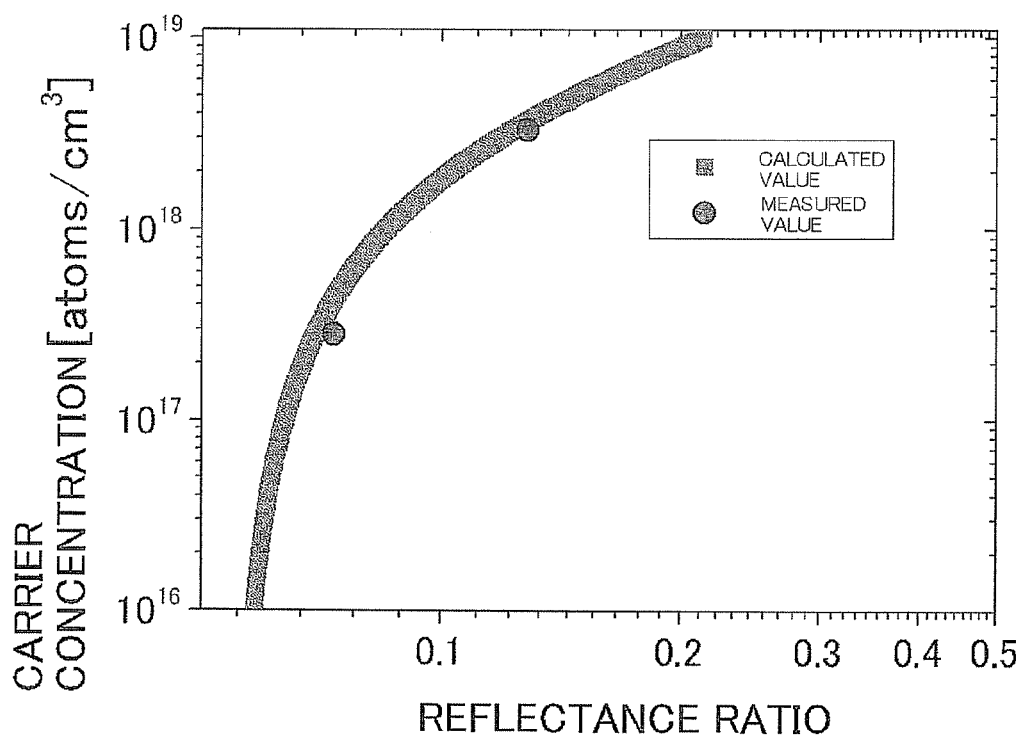
FIG. 8 shows the calculated values and the measured values of the reflectance and the carrier concentration of SiC.

FIG. 8 shows the calculated values and the measured values of the reflectance ratio and the carrier concentration of SiC. In the graph shown in FIG. 8, the abscissa axis indicates the reflectance ratio, and the ordinate axis indicates the carrier concentration [atoms/cm$^3$]. FIG. 8 shows the calculated values of the carrier concentration with respect to the reflectance ratios that are determined by comparing the reflectance of a light wave of a terahertz wave from a high-reflection band (the reference band) with the reflectance of a light wave of terahertz light from a band (the measurement band) in which the reflectance varies with the carrier concentration, and the hole measured values. The carrier concentration determined from the measured reflectance matches the carrier concentration determined by hole measurement.

Example 3

The carrier concentration of GaAs was measured with the use of the carrier concentration measuring device illustrated in FIG. 2. The shape of each used sample in a plan view is equal to or more than 10 mm square and equal to or less than 15 mm square having a thickness of equal to or more than 0.3 mm and equal to or less than 1.0 mm. The used samples are as-grown crystals that have carrier concentrations of $3.2 \times 10^{15}$ [atoms/cm$^3$] and $4.0 \times 10^{17}$ [atoms/cm$^3$].

Figure 9:
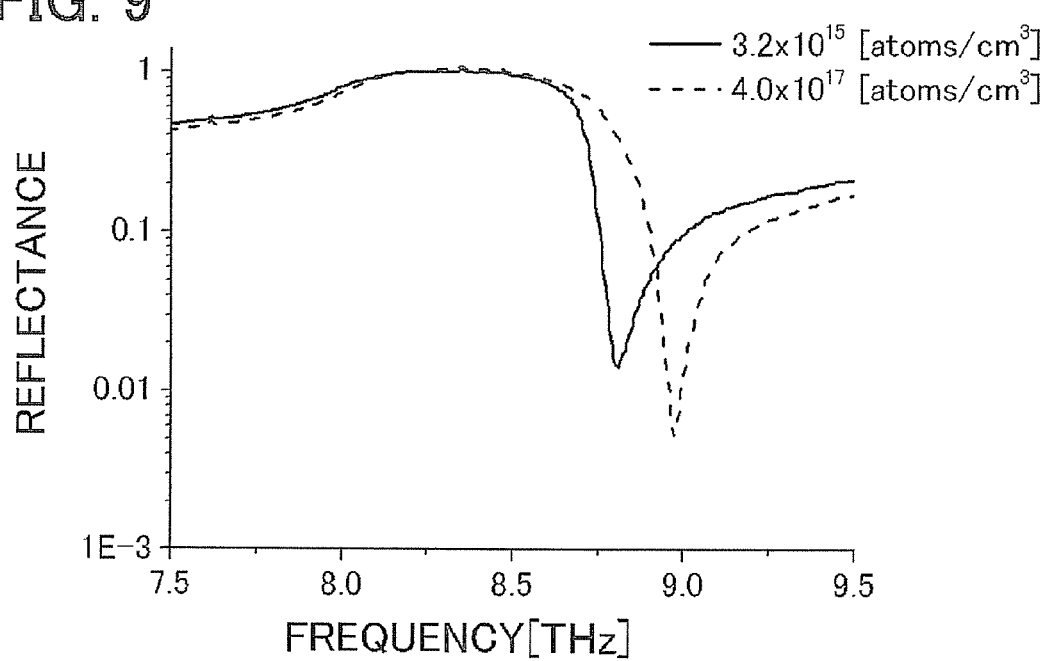
FIG. 9 shows the results of measurement of the reflectance of GaAs to frequency.

FIG. 9 shows the results of measurement of the reflectance of GaAs against frequency. In the graph shown in FIG. 9, the abscissa axis indicates the frequency [THz], and the ordinate axis indicates the reflectance. The results of measurement carried out on GaAs having the carrier concentrations of $3.2 \times 10^{15}$ and $4.0 \times 10^{17}$ [atoms/cm$^3$] are shown in the graph of FIG. 9. High reflection is observed in equal to or more than 8.2 THz and equal to or less than 8.5 THz. The reflectance varies with changes in carrier concentration in equal to or more than 8.6 THz and equal to or less than 8.8 THz. Therefore, the measurement band was set equal to or more than 8.6 THz and equal to or less than 8.8 THz, and the reference band was set equal to or more than 8.2 THz and equal to or less than 8.5 THz.

Figure 10:
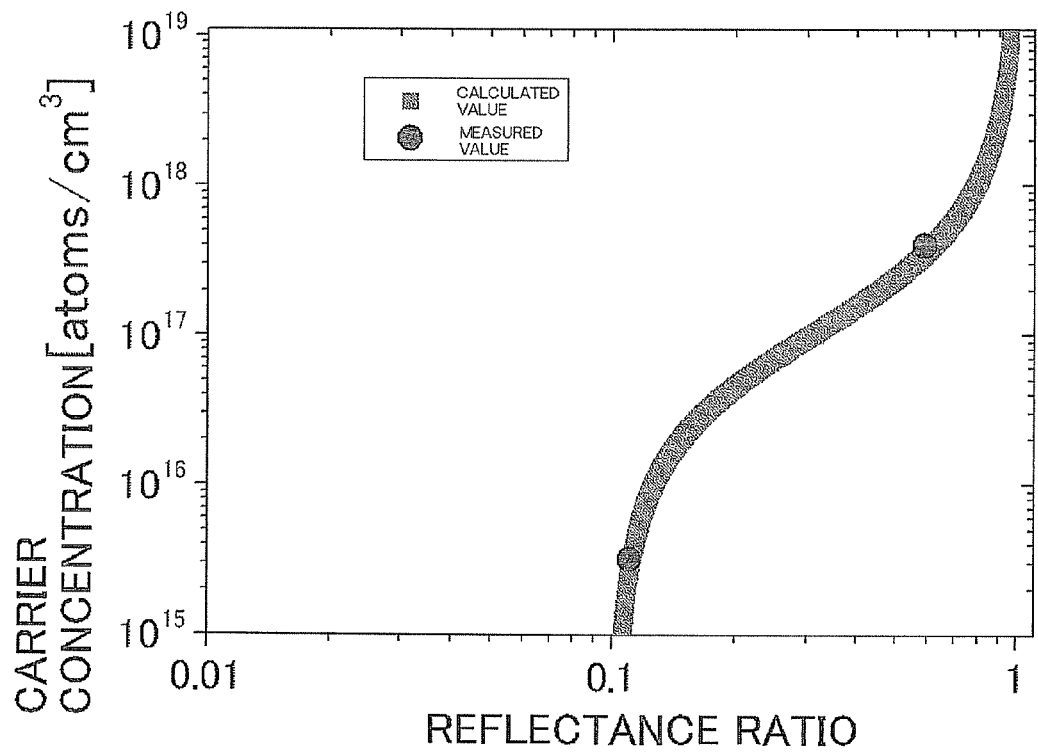
FIG. 10 shows the calculated values and the measured values of the reflectance and the carrier concentration of GaAs.

FIG. 10 shows the calculated values and the measured values of the reflectance ratio and the carrier concentration of GaAs. In the graph shown in FIG. 10, the abscissa axis indicates the reflectance ratio, and the ordinate axis indicates the carrier concentration [atoms/cm$^3$]. FIG. 10 shows the calculated values of the carrier concentration with respect to the reflectance ratios that are determined by comparing the reflectance of a light wave of a terahertz wave from a high-reflection band (the reference band) with the reflectance of a light wave of terahertz light from a band (the measurement band) in which the reflectance varies with the carrier concentration, and the hole measured values. The carrier concentration determined from the measured reflectance matches the carrier concentration determined by hole measurement.

Example 4

Figure 11:
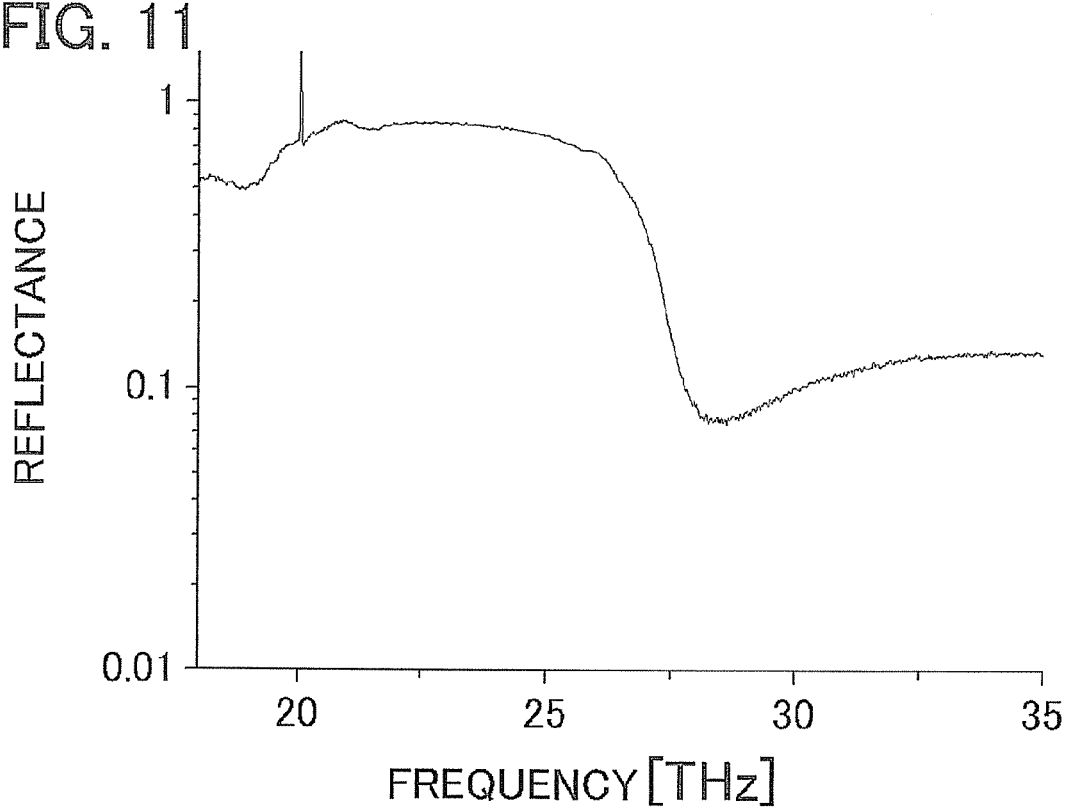
FIG. 11 shows the results of measurement of the reflectance of AlGaN to frequency.
Figure 12:
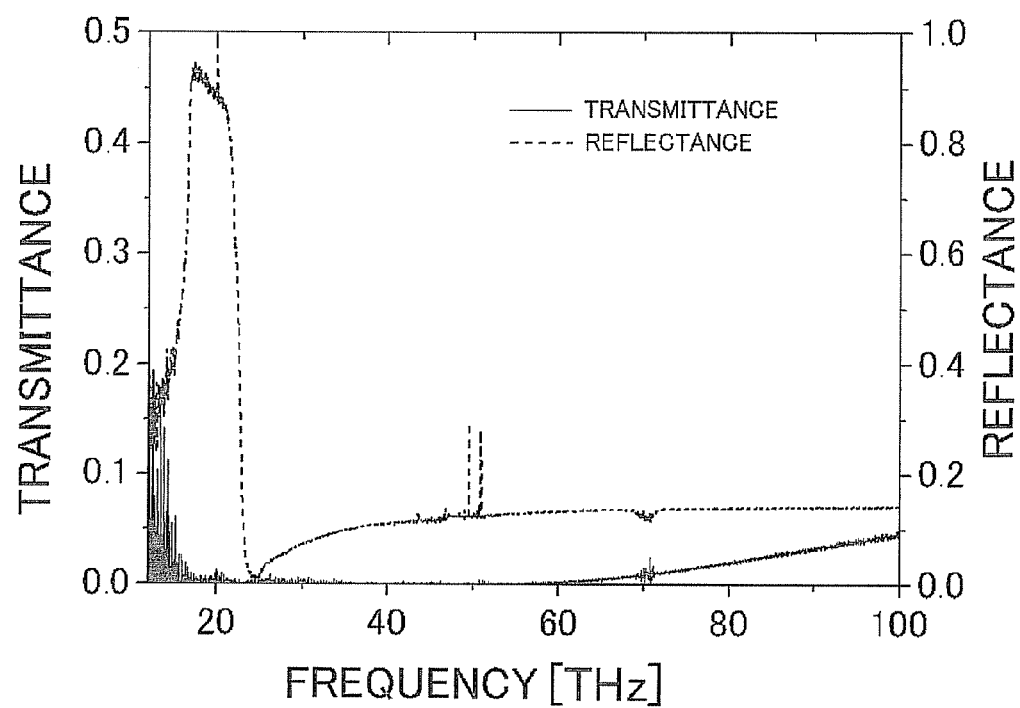
FIG. 12 shows the results of measurement of the transmittance and reflectance of GaN.

The carrier concentration of AlGaN was measured with the use of the carrier concentration measuring device illustrated in FIG. 2. The shape of each used sample in a plan view is equal to or more than 10 mm square and equal to or less than 15 mm square having a thickness of 5 µm. FIG. 11 shows the results of measurement of the reflectance of AlGaN against frequency. In the graph shown in FIG. 11, the abscissa axis indicates the frequency [THz], and the ordinate axis indicates the reflectance. As shown in FIG. 11, a variation in the reflectance is also observed in AlGaN. Accordingly, carrier concentrations can be calculated by measuring the reflectance of each of samples having different carrier concentrations.

The invention claimed is:

1. A carrier concentration measuring device that measures a carrier concentration of an impurity-doped inorganic compound semiconductor, comprising:
   a light radiation unit that irradiates the terahertz light to said inorganic compound semiconductor as a sample;
   a detection unit that detects reflected light of said inorganic compound semiconductor against said irradiated terahertz light;
   a computer containing storage that stores a correlation between reflectance of said inorganic compound semiconductor against terahertz light and said carrier concentration;
   said computer containing a processor that calculates an actual measurement value of the reflectance of said inorganic compound semiconductor by determining a ratio of intensity of said reflected light to intensity of said irradiated terahertz light, and refers to said stored correlation and reads the carrier concentration of said sample corresponding to the actual measurement value of said reflectance, wherein said processor sets measured reflectance as said reflectance against terahertz light of a measurement band in which the reflectance of said inorganic compound semiconductor against said terahertz light varies depending on said carrier concentration, said processor sets reference reflectance as said reflectance against terahertz light of a reference band in which said reflectance of said inorganic compound semiconductor against said terahertz light does not vary depending on said carrier concentration, said processor calculates a predicted reflectance ratio by comparing said measured reflectance with said reference reflectance, and said computer containing further storage that stores a correlation between said predicted reflectance ratio and said carrier concentration.

2. The carrier concentration measuring device as claimed in claim 1, wherein said light radiation unit irradiates terahertz light of equal to or more than 1.5 THz and equal to or less than 40 THz.

3. The carrier concentration measuring device as claimed in claim 1, wherein permittivity of said inorganic compound semiconductor is calculated from said carrier concentration, predicted reflectance is calculated from said calculated permittivity, and a correlation between said predicted reflectance and said carrier concentration is stored in said computer containing storage.

4. The carrier concentration measuring device as claimed in claim 1, wherein said inorganic compound semiconductor is one of gallium nitride, silicon carbide, and gallium arsenide.

5. The carrier concentration measuring device as claimed in claim 1, wherein said light radiation unit includes DAST crystals.

6. The carrier concentration measuring device as claimed in claim 1, wherein said light radiation unit irradiates terahertz light of said measurement band and terahertz light of said reference band to said sample, said processor calculates an actual measurement value of a reflectance ratio by comparing said reflectance calculated when the terahertz light of said measurement band is irradiated with said reflectance calculated when the terahertz light of said reference band is irradiated, and said processor refers to said stored correlation between said predicted reflectance ratio and said carrier concentration, and reads said carrier concentration corresponding to the calculated actual measurement value of said reflectance ratio.

7. The carrier concentration measuring device as claimed in claim 1, wherein said reference band is a high-reflection band between TO phonon frequency and LO phonon frequency.

8. The carrier concentration measuring device as claimed in claim 1, wherein said inorganic compound semiconductor is gallium nitride, said measurement band is equal to or more than 1 THz and equal to or less than 16 THz or equal to or more than 21 THz and equal to or less than 23 THz, and said reference band is equal to or more than 17 THz and equal to or less than 20 THz.

9. The carrier concentration measuring device as claimed in claim 1, wherein said inorganic compound semiconductor is silicon carbide, said measurement band is equal to or more than 28 THz and equal to or less than 30 THz, and said reference band is equal to or more than 25 THz and equal to or less than 27 THz.

10. The carrier concentration measuring device as claimed in claim 1, wherein said inorganic compound semiconductor is gallium arsenide, said measurement band is equal to or more than 8.6 THz and equal to or less than 8.8 THz, and said reference band is equal to or more than 8.2 and equal to or less than 8.5 THz.

11. A carrier concentration measuring method for measuring a carrier concentration of an impurity-doped inorganic compound semiconductor, comprising:

acquiring a correlation between reflectance of said inorganic compound semiconductor against terahertz light and said carrier concentration;

irradiating the terahertz light to said inorganic compound semiconductor as a sample;

detecting reflected light of said inorganic compound semiconductor against said irradiated terahertz light;

calculating an actual measurement value of the reflectance of said inorganic compound semiconductor by determining a ratio of intensity of said reflected light to intensity of said irradiated terahertz light; and reading the carrier concentration of said sample corresponding to the actual measurement value of said reflectance calculated, by referring to said stored correlation, wherein said reflectance against terahertz light of a measurement band in which the reflectance of said inorganic compound semiconductor against said terahertz light varies depending on said carrier concentration is set as measured reflectance, said reflectance against terahertz light of a reference band in which said reflectance of said inorganic compound semiconductor against said terahertz light does not vary depending on said carrier concentration is set as reference reflectance, a predicted reflectance ratio is calculated by comparing said measured reflectance with said reference reflectance, and a correlation between said predicted reflectance ratio and said carrier concentration is obtained.

12. The carrier concentration measuring method as claimed in claim 11, wherein said irradiating the terahertz light includes irradiating terahertz light of equal to or more than 1.5 THz and equal to or less than 40 THz.

13. The carrier concentration measuring method as claimed in claim 11, wherein said irradiating the terahertz light includes irradiating terahertz light of said measurement band and terahertz light of said reference band to said sample, said calculating the measured value of the reflectance of said inorganic compound semiconductor includes calculating an actual measurement value of a reflectance ratio by comparing said reflectance calculated when the terahertz light of said measurement band is irradiated with said reflectance calculated when the terahertz light of said reference band is irradiated, and said reading the carrier concentration of said sample includes referring to said obtained correlation between said predicted reflectance ratio and said carrier concentration, and reading said carrier concentration corresponding to the calculated actual measurement value of said reflectance ratio.

14. The carrier concentration measuring method as claimed in claim 11, wherein said reference band is a high-reflection band between TO phonon frequency and LO phonon frequency.

15. The carrier concentration measuring method as claimed in claim 11, wherein
    said inorganic compound semiconductor is gallium nitride,
    said measurement band is equal to or more than 1 THz and equal to or less than 16 THz or equal to or more than 21 THz and equal to or less than 23 THz, and
    said reference band is equal to or more than 17 THz and equal to or less than 20 THz.

16. The carrier concentration measuring method as claimed in claim 11, wherein
    said inorganic compound semiconductor is silicon carbide,
    said measurement band is equal to or more than 28 THz and equal to or less than 30 THz, and
    said reference band is equal to or more than 25 THz and equal to or less than 27 THz.

17. The carrier concentration measuring method as claimed in claim 11, wherein
    said inorganic compound semiconductor is gallium arsenide,
    said measurement band is equal to or more than 8.6 THz and equal to or less than 8.8 THz, and
    said reference band is equal to or more than 8.2 THz and equal to or less than 8.5 THz.

\* \* \* \* \*